United States Patent [19]

Skocypec et al.

[11] 3,989,461
[45] Nov. 2, 1976

[54] APPARATUS FOR USE, RECOVERY, RECONSTITUTION, AND RECYCLIZATION OF STERILANT GAS MIXTURE

[75] Inventors: Russell Skocypec, Homewood; Joseph C. Crowther, Jr., Hazel Crest; Richard J. Cimaroli, South Holland, all of Ill.

[73] Assignee: Vacudynealtair, Inc., Chicago Heights, Ill.

[22] Filed: Mar. 3, 1975

[21] Appl. No.: 554,540

[52] U.S. Cl. .................................. 21/91; 21/103; 21/DIG. 4
[51] Int. Cl.² .................. A61L 3/00; A61L 3/02; A61L 13/00
[58] Field of Search ................ 21/91–93, 21/103, DIG. 4, 58

[56] References Cited
UNITED STATES PATENTS

| | | | |
|---|---|---|---|
| 2,080,179 | 5/1937 | Merriam et al. | 21/58 |
| 2,131,134 | 9/1938 | Baer et al. | 21/58 |
| 2,370,768 | 3/1945 | Baerwald | 21/58 UX |
| 3,372,980 | 3/1968 | Satas | 21/58 |
| 3,549,312 | 12/1970 | Ernst | 21/58 |
| 3,598,517 | 8/1971 | Beecher | 21/103 X |

*Primary Examiner*—Morris O. Wolk
*Assistant Examiner*—Bradley R. Garris
*Attorney, Agent, or Firm*—Kegan, Kegan & Berkman

[57] ABSTRACT

Apparatus and method for the recovery, reconstitution and recyclization of a gaseous mixture used as a sterilizing medium. A recycle line interconnects a gas condenser with a sterilization chamber to return a portion of the gases discharged from the chamber, thus avoiding excessive gas losses through venting and ensuring that the pressure in the chamber remains above a selectable predetermined minimum. This eliminates the need for a vacuum pump and obviates expansive explosion of sealed packages contained in the sterilization chamber. The system also uses a liquid ring compressor provided with a special liquid sealant comprising a polyhydric alcohol.

8 Claims, 1 Drawing Figure

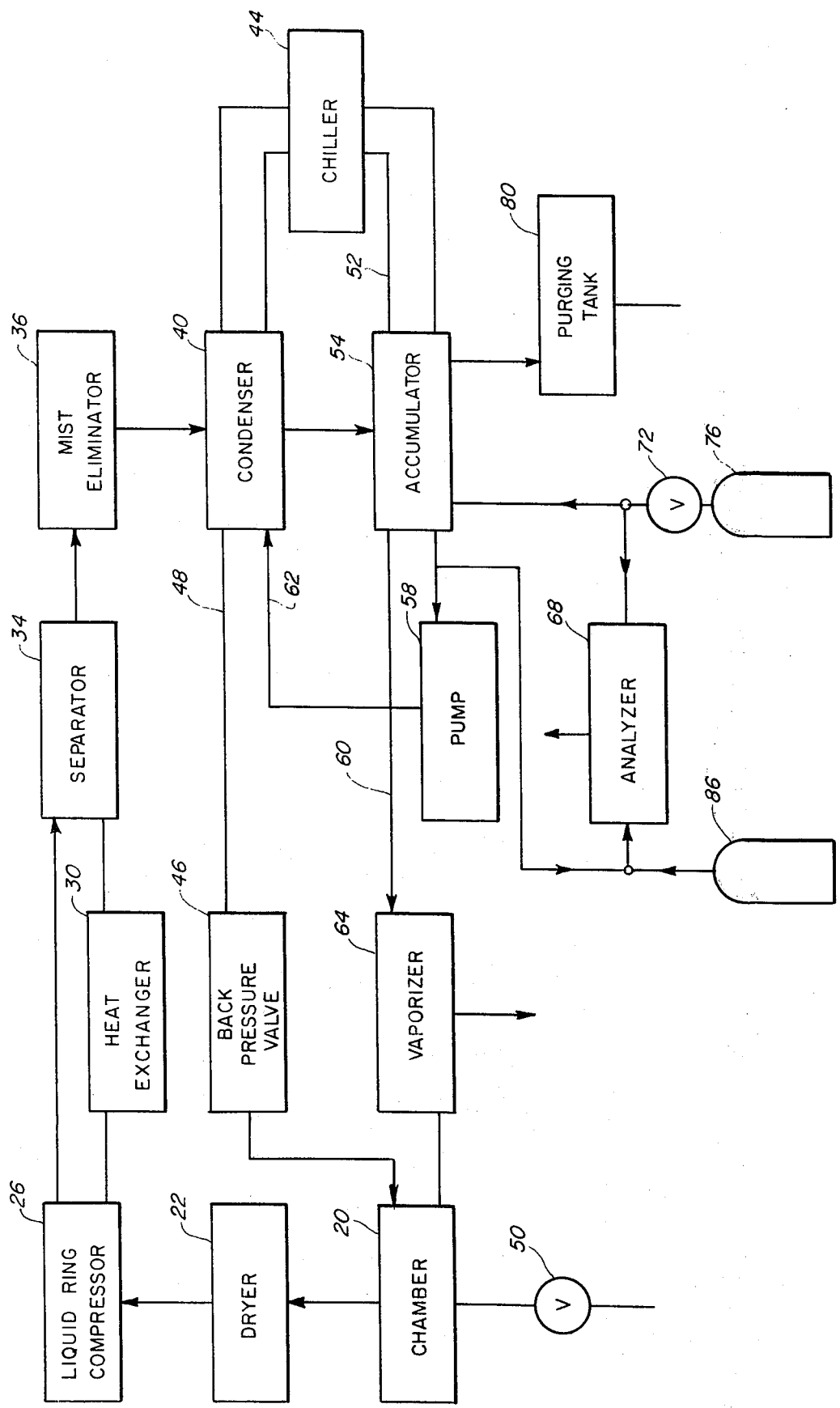

APPARATUS FOR USE, RECOVERY, RECONSTITUTION, AND RECYCLIZATION OF STERILANT GAS MIXTURE

BACKGROUND OF THE INVENTION

The use of a sterilizing or biocidal gas or a mixture of gases as a sterilization medium is well established in the prior art. Such gaseous atmospheres are highly effective in de-activating and destroying viable micro-organisms and insects as well as life-cycle forms through which such organisms evolve.

Gaseous sterilization systems of the type contemplated and utilized in the present invention are "non-destructive". Autoclaving caustics, corrosive agents, and other deleterious agents and techniques are avoided. Accordingly, the procedures of the invention are specially adapted to the treatment of perishable substances such as foodstuffs, agricultural products, and pharmaceuticals as well as the sterilization of intricate and costly hospital equipment including surgical instruments and apparatus.

Alkylene oxides are dxsensively used as non-corrosive gaseous sterilizing agents; the most commonly used are ethylene oxide and propylene oxide. These compounds destroy many types of objectionable organisms, remain gaseous at relatively low temperatures, are non-corrosive, and are essentially non-destructive with respect to sensitive and delicate metals and many other materials including plastics, rubber, adhesives, comestibles, and drugs. Alkylene oxides are ordinarily diluted with an inert gas such as a halogenated hydrocarbon or with carbon dioxide to eliminate flammability. A commercially available mixture consisting of about 12% by weight of ethylene oxide mixed with 88% by weight of a halogenated hydrocarbon such as dichloro difluoromethane (Freon 12) is a preferred formulation. Other "inert" halogenated hydrocarbons marketed under the trademarks FREONS, UCONS, and GENETRONS may be used as diluents for the ethylene oxide to obviate flammability and to prevent the development of explosive atmospheres.

Until relatively recently, the sterilization technique adapted has been to place the articles or materials to be treated in a tank or sterilization chamber and then to introduce a prescribed composition of sterilant into the chamber at controlled temperatures and pressures. After a predetermined, selectible dwell time, the sterilant gas was pumped from the chamber and discarded into the atmosphere. Finally, the chamber was swept with filtered air. No effort was made to reclaim the sterilant mixtures for re-use.

However, with the marked increased in materials cost, and with recognition of ecological problems posed by indiscriminate discharge of the ethylene oxide and the halogenated hydrocarbons into the air, new techniques have been devised. After use, the gaseous mixture is recovered to be used again. In the new processes, the concentrations of components in the gaseous mixture are readjusted prior to re-use. An example of the re-use of sterilizing gas (steam) through recovery, condensation, and recyclization in a closed system is described in Skaller U.S. Pat. No. 3,361,517. Satas U.S. Pat. No. 3,372,980 describes ethylene oxide recyclization in a gaseous sterilization system and suggests the periodic refortification of the gas mixture by addition of pure ethylene oxide. Ernst U.S. Pat. No. 3,549,312 also describes recovery and condensation of a sterilizing gas for re-use, and maintenance of the desired mixture through addition of the "inert" diluent, as required to reconstitute the mixture to the desired concentrational composition.

Notwithstanding extensive research and development in the field of gaseous sterilization, particularly in recovery and re-use of the sterilizing agents, no completely satisfactory apparatus or process has heretofore been achieved. Each of the prior art procedures suffers from deficiencies or shortcomings which have impaired general usefulness and have precluded adoption by the industry. It is, accordingly, the aim of the present invention to provide an improved process and apparatus whereby the recovery and re-use of sterilization gas atmospheres may be safely, effectively, and economically carried out.

SUMMARY OF THE INVENTION

The present invention relates to processing apparatus and a method for utilizing such apparatus in the gaseous sterilization of materials and equipment. It is a principal feature of the invention that there is provided, in conjunction with a condenser for converting the gaseous mixture removed from the reaction chamber into a liquid phase, a novel recycle line interconnecting the condenser back to the reaction chamber itself. Losses of processing sterilization gas are minimized, and a minimum pressure is maintained in the reaction chamber to obviate expansive explosion of any sealed packages contained therein.

An additional novel feature of the invention is an improved compressor system employing a liquid ring type compressor which utilizes as the liquid sealant a material substantially inert to the sterilization gas mixture, and preferably consisting of a polyhydric alcohol such as ethylene glycol or propylene glycol.

Still another feature of the invention is the utilization, in conjunction with the gas condenser and with the accumulator into which the condenser delivers its liquid phase condensate, of a chilling or cooling unit capable of accommodating load variation which occurs during the gaseous reclamation process.

Yet another feature of the invention is a pump which operates between the accumulator and the condenser to return a portion of the condensed sterilant to the condenser to impinge upon the condenser coils thereby to wash therefrom any noncondensible film which forms.

A related feature of the invention is use of a condenser. The condensate which forms falls into a precooled accumulator, and a portion of the remaining vapor consisting of air containing an equilibrium concentration of sterilant gas is returned to the sterilization chamber through the recycle line.

An important feature of the improved apparatus of the invention is the utilization of a liquid ring compressor which is sealed with recirculating ehtylene glycol (or other polyhydric alcohol) to provide the vapor phase motive power, while maintaining hydrolysis of sterilant itself.

Another feature of the improved process is the utilization of a gas analyzer which operates automatically as an intermittant sampling device and regulates the addition of inert diluent to the alkylene oxide sterilizing gas, as is required after each reclamation to readjust the gaseous mixture to its original composition.

Still another feature of the apparatus of the invention is the utilization of a vaporizer in the line between the accumulator and the reaction chamber, and discharge means whereby the non-volatile material may be purged after each use of the sterilant gas mixture.

A practical feature imparting valuable versatility to the invention is that, in a preferred embodiment, the apparatus is a self-contained, separate assembly adapted for ready connection to and operation with existing gas sterilization equipment to convert such equipment to apparatus capable of recyclization and re-use of gaseous sterilant.

Other and further objects, advantages, and features of the invention will become apparent from a consideration of the specification in conjunction with the drawings.

DESCRIPTION OF THE DRAWING

The drawing is a schematic illustration of the gas sterilization and recovery and re-use system, in accordance with the invention.

DESCRIPTION OF THE PREFERRED EMBODIMENT

The subject invention is directed to an improved gas reclamation system utilizing a self-contained unit effective to recover for re-use the majority of a commercial sterilant gas such as 12–88 gas (12% ehtylene oxide and 88% diluent, such as dichlorodifluoromethane). Briefly, after its functional use in a sterilization chamber, the sterilant gas mixture is pumped from the chamber, dried, compressed, cooled and condensed, fortified or reconstituted, and then redirected into the reaction chamber for re-use. In the following paragraphs, each unit process will be considered in turn and important novel features of each step pointed out with reference to the drawing.

Drying

After a predetermined dwell period at selectible temperatures and pressures in the reaction chamber 20, the sterilant gas mixture is discharged to enter a dryer 22 which may be any suitable type but which is, in the preferred embodiment of the invention, a vessel filled with a desiccant. After each reclamation cycle, heated air is passed through the dryer to remove accumulated water and to recondition the desiccant. It will be appreciated that when its efficiency has been objectionably impaired, the desiccant is discarded and replaced with new material.

Compression

The dry gaseous mixture enters a liquid ring compressor 26 utilizing recirculating polyhydric alcohol such as ethylene glycol or propylene glycol. Since the alkylene oxide fraction of the sterilant gas is particularly sensitive to heat and may undergo adverse chemical reactions such as polymerization, a liquid ring compressor is functionally advantageous in that it facilitates establishing intimate heat-exchanging contact between the gas and the circulating liquid of the compressor. The liquid itself is cooled externally of the compressor 26 in a heat exchanger 30. Since the alkylene oxide-halogenated hydrocarbon mixture and the glycol are essentially unreactive with one another, no gas is expelled as waste. Additionally, the glycol is effective to minimize hydrolysis of the alkylene oxide by whatever residual water may be retained in the gas. Objectional chemical side reactions are also avoided. The heat-exchanger 30 and the associated control system maintain the glycol termperature at a value which eliminates gross condensation of sterilant in the compressor 26. The gas from the liquid ring compressor 26 then passes through a gas-liquid separator 34.

Condensation

The gas discharged from the separator 34 goes through a mist eliminator 36 which prevents the mechanical carry-over of entrained glycol from the separator into the condenser 40. The condenser operates at fixed temperature and pressure controlled respectively by a chiller 44 and a back pressure valve 46. The back pressure release gas consisting of air and uncondensed diluent-rich sterilant is recycled to the sterilizer chamber 20 through a recycle line 48. This recycle circuit is a very important feature of the present invention and has several critical functions. First, if the condenser 40 does not operate near equilibrium conditions, the amount of sterilant which would be lost if the gas were vented could be quite significant. Second, even if the condenser 40 were to operate near equilibrium conditions, some non-condensable gas would have to be bled into the chamber during reclamation if the product being sterilized could not withstand deep vacuum. Such conditions would exist if the contents of the sterilization chamber 20 included articles prepackaged and sealed in semi-permeable sheet material such as plastic film. The recycle circuit also obviates any need for a vacuum pump or equivalent device, and ensures that the final pressure in the evacuation chamber 20 does not fall below a minimum predetermined value.

An air inbleed valve 50, connected to the chamber 20, is provided for use under conditions of operation in which the initial vacuum drawn on the chamber 20 is greater than that which the compressor 26 is capable of producing during the sterilant reclamation process.

The chiller unit 44 provides a circulating cooled ethylene glycol-water mixture which is delivered to the condenser 40 as a cooling medium. Additionally, the chiller 44 includes a cooling line 52 through which the cooled ethylene glycol-water mixture is also delivered to an accumulator 54 which receives the liquid condensate from the condenser 40.

In order further to improve condenser efficiency, a pump 58 delivers a portion of the condensed sterilant from the accumulator 54 to the condenser 40 through a line 62, the liquid being directed to the condenser coils to wash off any noncondensable film which may form.

Composition of Reclamate

Since the gas recycled from the condenser 40 to the reaction chamber 20 is of a different composition from the original chamber gas, the gas mixture which enters the condenser 40 is of a contiuously changing composition. Nevertheless, the liquid which condenses and is delivered to the accumulator 54 is of a constant composition throughout the reclamation cycle provided the condenser operates near equilibrium conditions. The condenser initially produces a saturated liquid and a saturated vapor. If this vapor is recycled to the reaction chamber 20, the new mixture which the condenser sees acts as if it were part totally inert diluent and part original chamber gas. That is, the recycled saturated vapor portion continues to behave as a saturated vapor, neither adding to nor extracting from the other materials in the condenser. The original chamber gas portion produces additional saturated liquid and vapor.

Analysis and Reblending

Responsive to programming controls (not shown), when the sterilant has been condensed and delivered to the accumulator 54 the sterilizing chamber 20 is ready to enter upon a new cycle. In order to ensure that the sterilizing gas delivered from the accumulator 54 to the chamber 20 through a conduit 60 and an intermediate vaporizer 64 has the proper composition, a portion of the condensate from the accumulator 54 is delivered to an analyzer 68. The analyzer 68 is an intermittant sampling conductivity device. Since thermodynamics dictate that the reclamate in the accumulator 54 will be rich in ethylene oxide, and that, accordingly, additional diluent is required to establish the original concentrational composition, responsive to the concentration sensed and read by the analyzer 68, the analyzer operates and opens a control valve 72 which allows diluent contained in a supply cylinder 76 to be delivered to the accumulator 54 for blending with the contents thereof. The analysis and control of the diluent input continue until the analyzer 68 senses that the required concentrational composition has been reached in the accumulator 54. The reblended liquid remains in the accumulator 54 until the sterilizer 20 reaches the gassing phase of its next cycle.

Re-gassing

Since the reclaimed sterilant stored in the accumulator 54 may contain some polymer, glycol, or other liquid contaminant, the accumulator 54 is provided with a tank 80 with automatic purging capability, whereby floating matter is purged from the accumulator 54 after each use and is discarded.

The liquid sterilant is delivered from the accumulator 54 to the vaporizer 64 when the liquid is transformed into gas for return to the chamber 20. The vaporizer 64 is also provided with self purging capabilities so that non-volatiles may be voided.

As indicated in the schematic drawing, a tank 86 containing the "12–88" composition used in the sterilization chamber 20 is connected as a standardizing supply to the analyzer 68.

The apparatus of the above described system utilizes suitable control instrumentation including an analyzer readout meter relay, a precool timer, audible and visual alarms, pilot lights to indicate cycle phase, and all necessary switches and controls. All circuitry wiring and control enclosures are designed with safety and simplicity in mind. Since the controls are of the type well known to those skilled in this art, no detailed description is included herein.

While the present invention has been described with reference to a specific sterilant reclamation device consisting of a self-contained unit, and while a particular form of the invention has been shown and described, it is to be understood that the disclosure is directed to a preferred embodiment. It will occur to those skilled in the art that various changes and modifications may be restored to without departing from the concept of the invention, or the ambit of the sub-joined claims. All such modifications and variations are deemed to fall within the scope of the subject invention.

What is claimed is:

1. Apparatus for the gaseous sterilization of articles comprising a sterilizing chamber for containing the articles and a gaseous sterilizing agent for controlled exposure of said articles thereto, means for introducing said gaseous sterilizing agent into and means for evacuating said gaseous agent from said chamber, condenser means for converting gas discharged from said chamber into a liquid phase for storage, reconstitution and reintroduction into and re-use in said chamber, and gas recycle conduit means interconnecting said condenser means with said chamber to return to said chamber, throughout a sterilant reclamation cycle, a portion of gases discharged from the chamber and delivered to said condenser means, said portion of gases including all non-condensable gases as well as sterilant gases not condensed under the operating conditions of said condenser means, thereby to preclude excessive gas losses through venting at said condenser means, and to maintain gaseous pressure in said chamber during evacuation thereof above a selectable predetermined minimum value, whereby expansive explosion of articles contained is said chamber during evacuation is precluded, and whereby any need for auxiliary vacuum producing apparatus is obviated.

2. In an apparatus for gaseous sterilization and including a treatment chamber for containing articles and an alkylene oxide gaseous sterilizing agent for controlled exposure of said articles to said agent, means for introducing said sterilizing agent into and means for discharging said sterilizing agent from said chamber, condenser means for converting gas discharged from said chamber into a liquid phase for storage, reconstitution and reintroduction into and re-use in said chamber, the improvement wherein said condenser means includes a liquid ring compressor having a liquid sealant comprising a polyhydric alcohol.

3. A device for reclaiming gaseous sterilant from a gas sterilization chamber, for reconstituting the reclaimed sterilant to a predetermined concentrational composition, and for recycling the reconstituted sterilant to the chamber for re-use, said device comprising chamber evacuation means and conduit means for attaching said evacuation means to the chamber, said evacuation means including gas compressor means and condenser means for converting evacuated gaseous sterilant to a liquid phase, gas-recycle conduit means for interconnecting a vapor supply from said condenser means to the chamber to return to the chamber a portion of the gaseous sterilant evacuated therefrom so as to minimize losses of sterilant from said condenser means, and also to maintain the pressure within the chamber above a predetermined minimum so as to obviate expansive explosion of articles contained in the chamber, gas vaporizing means and fluid conducting means interconnecting said gas vaporizing means with said condenser means, the interconnecting being for delivery to said gas vaporizing means of a liquid phase produced in said condenser means, and conduit means connecting an output from said gas vaporizing means to the chamber to re-cycle reclaimed sterilant gas thereto.

4. The device as set forth in claim 3 and further comprising
storage means for retaining liquid sterilant recovered from said condenser means,
gas analyzer means operatively connected to said storage means for periodically assaying the recovered liquid phase sterilant contained in said storage means, to sense quantitatively the composition thereof, and
diluent supply means responsive to said analyzer means, upon demand, to add diluent to the recovered sterilant so as to attain a predetermined desired concentrational composition.

5. The device as set forth in claim 4 wherein the gaseous sterilant is a mixture of alkylene oxide and an inert diluent, and wherein said diluent supply means comprises a pressurized container of inert diluent for reducing the concentration of alkylene oxide in the liquid phase sterilant preparatory to vaporization of the liquid phase sterilant for recyclization to the sterilization chamber.

6. In apparatus for the gaseous sterilization of articles, including:
a sterilizing chamber for containing the articles and a gaseous sterilizing agent for controlled exposure of said articles thereto,
means for introducing said gaseous sterilizing agent into and means for evacuating said gaseous agent from said chamber, and
condenser means for converting gas discharged from said chamber into a liquid phase for storage, reconstitution and reintroduction into and re-use in said chamber,
the improvement comprising gas recycle conduit means interconnecting said condenser means with said chamber to return to said chamber, throughout a sterilant reclamation cycle, a portion of gases discharged from the chamber and delivered to said condenser means,
said portion of gases including all non-condensable gases and sterilant gases not condensed under the operating conditions of said condenser means, thereby to preclude excessive gas losses through venting at said condenser means, and to maintain gaseous pressure in said chamber during evacuation thereof above a selectable predetermined minimum value,
whereby expansive explosion of articles contained in said chamber during evacuation is precluded, and whereby any need for auxiliary vacuum producing apparatus is obviated.

7. A device for reclaiming gaseous sterilant from a gas sterilization chamber, for reconstituting the reclaimed sterilant to a predetermined concentrational composition, and for recycling the reconstituted sterilant to the chamber for re-use, said device comprising
chamber evacuation means and conduit means for attaching said evacuation means to the chamber,
said evacuation means including gas compressor means and condensor means for converting evacuated gaseous sterilant to a liquid phase,
gas re-cycle conduit means for interconnecting a vapor supply from said condenser means to the chamber to return to the chamber a portion of the gaseous sterilant evacuated therefrom so as to minimize losses of sterilant from said condenser means, and also to maintain the pressure within the chamber above a predetermined minimum so as to obviate expansive explosion of articles contained in the chamber,
gas vaporizing means and fluid conducting means interconnecting said gas vaporizing means with said condenser means, the interconnecting being for delivery to said gas vaporizing means of a liquid phase produced in said condenser means,
conduit means connecting an output from said gas vaporizing means to the chamber to re-cycle reclaimed sterilant gas thereto,
said gaseous sterilant being an alkylene oxide and said compressor means comprising a liquid ring compressor having a liquid sealant consisting essentially of a polyhydric alcohol,
thereby to reduce any hydrolysis of the gaseous sterilant in the fluid sealant of said liquid ring compressor and to obviate substantial chemical interaction between the fluid sealant and the gaseous sterilant.

8. Apparatus for the gaseous sterilization of articles comprising
a sterilizing chamber for containing the articles and a gaseous sterilizing agent for controlled exposure of said articles thereto,
means for introducing said gaseous sterilizing agent into and means for evacuating said gaseous agent from said chamber,
condenser means for converting gas discharged from said chamber into a liquid phase for storage, reconstitution and reintroduction into and re-use in said chamber, and
gas recycle conduit means interconnecting said condenser means with said chamber to return to said chamber, throughout a sterilant reclamation cycle, a portion of gases discharged from the chamber and delivered to said condenser means, said portion of gases including all non-condensable gases as well as sterilant gases not condensed under the operating conditions of said condenser means, thereby to preclude excessive gas losses through venting at said condenser means, and to maintain gaseous pressure in said chamber during evacuation thereof above a selectable predetermined minimum value,
whereby expansive explosion of articles contained in said chamber during evacuation is precluded, and whereby any need for auxiliary vacuum producing apparatus is obviated,
said condenser means including condenser coils and a condensate discharge means, and
pump means operatively connected to said discharge means to return a portion of the condensate to said condenser means to impinge on said condenser coils thereof, thereby to wash from the outer surface of said coils any non-condensable film deposited thereon.

* * * * *